US00PP19932P2

(12) United States Plant Patent
Bennett

(10) Patent No.: US PP19,932 P2
(45) Date of Patent: Apr. 21, 2009

(54) ***COREOPSIS* PLANT NAMED 'COREOPRAM'**

(50) Latin Name: ***Coreopsis rosea*×*Coreopsis verticillata***
Varietal Denomination: Coreopram

(75) Inventor: Andrew Paul Bennett, Cheltenham (GB)

(73) Assignee: R. A. Meredith & Son Ltd., Saul, Gloucester (GB)

( * ) Notice: Subject to any disclaimer, the term of this patent is extended or adjusted under 35 U.S.C. 154(b) by 18 days.

(21) Appl. No.: 11/903,538

(22) Filed: Sep. 21, 2007

(51) Int. Cl.
*A01H 5/00* (2006.01)

(52) U.S. Cl. ..... Plt./417
(58) Field of Classification Search ..... Plt./417
See application file for complete search history.

*Primary Examiner*—Kent L Bell
(74) *Attorney, Agent, or Firm*—C. A. Whealy

(57) ABSTRACT

A new and distinct cultivar of *Coreopsis* plant named 'Coreopram', characterized by its upright, outwardly spreading and mounded plant habit; vigorous growth habit; freely branching habit; freely flowering habit; and single inflorescences with dark red and yellow bi-colored ray florets.

1 Drawing Sheet

Botanical designation: *Coreopsis rosea*×*Coreopsis verticillata.*
Cultivar denomination: 'Coreopram'.

BACKGROUND OF THE INVENTION

The present invention relates to a new and distinct cultivar of *Coreopsis* plant, botanically known as *Coreopsis rosea*× *Coreopsis verticillata,* and hereinafter referred to by the name 'Coreopram'.

The new *Coreopsis* originated from a cross-pollination made by the Inventor in Saul, Gloucester, United Kingdom in July, 2002, of an unnamed selection of *Coreopsis rosea,* not patented, as the female, or seed, parent with an unnamed selection of *Coreopsis verticillata,* not patented, as the male, or pollen, parent. The new *Coreopsis* was discovered and selected by the Inventor as a single flowering plant from within the progeny of the stated cross-pollination grown in a controlled environment in Saul, Gloucester, United Kingdom in 2003.

Asexual reproduction of the new *Coreopsis* by vegetative cuttings in a controlled environment in Saul, Gloucester, United Kingdom since July, 2003, has shown that the unique features of this new *Coreopsis* are stable and reproduced true to type in successive generations.

SUMMARY OF THE INVENTION

The cultivar Coreopram has not been observed under all possible environmental conditions. The phenotype may vary somewhat with variations in environment such as temperature and light intensity, without, however, any variance in genotype.

The following traits have been repeatedly observed and are determined to be the unique characteristics of 'Coreopram'. These characteristics in combination distinguish 'Coreopram' as a new and distinct cultivar of *Coreopsis:*

1. Upright, outwardly spreading and mounded plant habit.
2. Vigorous growth habit.
3. Freely branching habit.

4. Freely flowering habit.
5. Single inflorescences with dark red and yellow bi-colored ray florets.

Plants of the new *Coreopsis* differ from plants of the female parent selection primarily in ray floret coloration as plants of the female parent selection have pink-colored ray florets.

Plants of the new *Coreopsis* differ from plants of the male parent selection primarily in ray floret coloration as plants of the male parent selection have yellow-colored ray florets.

Plants of the new *Coreopsis* can be compared to plants of the *Coreopsis* cultivar Sweet Dreams, disclosed in U.S. Plant Pat. No. 12,720. In side-by-side comparisons conducted in Saul, Gloucester, United Kingdom, plants of the new *Coreopsis* differed from plants of the cultivar Sweet Dreams primarily in ray floret coloration as plants of the cultivar Sweet Dreams have purple and white bi-colored ray florets.

BRIEF DESCRIPTION OF THE PHOTOGRAPHS

The accompanying photographs illustrate the overall appearance of the new *Coreopsis.* The photographs show the colors as true as it is reasonably possible to obtain in colored reproductions of this type. Colors in the photographs may differ slightly from the color values cited in the detailed botanical description which accurately describe the colors of the new *Coreopsis.*

The photograph at the bottom of the sheet comprises a side perspective view of a typical flowering plant of 'Coreopram' grown in a container.

The photograph at the top of the sheet is a close-up view of a typical inflorescence of 'Coreopram'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown one-gallon containers in Lancaster, Pa. during the winter and spring in a polyethylene-covered greenhouse and under conditions and practices which approximate those generally used in commercial *Coreopsis* production. During the production of the plants, day temperatures ranged from about 18° C. to 27° C. and night temperatures ranged from about 16° C. to 18° C. Measurements and numerical values represent averages for typical flowering plants. Plants were about six months old when the photographs and description were taken and had been pruned about five times.

Botanical classification: *Coreopsis rosea*×*Coreopsis verticillata* cultivar Coreopram.

Parentage:

*Female parent.*—Unnamed selection of *Coreopsis rosea,* not patented.

*Male parent.*—Unnamed selection of *Coreopsis verticillata,* not patented.

Propagation:

*Type.*—By vegetative cuttings.

*Time to initiate roots.*—About one week at 25° C.

*Time to produce a rooted young plant.*—About one month at 25° C.

*Root description.*—Thin, fibrous; color, 161B.

*Rooting habit.*—Freely branching; dense.

Plant description:

*Plant form/growth habit.*—Upright, outwardly spreading and mounding plant habit; broad inverted triangle; freely branching habit with about 12 to 14 lateral branches; inflorescences held above and beyond the foliage on moderately strong peduncles. Vigorous growth habit.

*Plant height.*—About 42 cm.

*Plant diameter or spread.*—About 38 cm.

*Lateral branches.*—Length: About 35 cm. Diameter: About 5 mm. Internode length: About 2.5 cm. Aspect: Mostly upright to outwardly spreading. Strength: Strong. Texture: Smooth, glabrous. Color: Close to 146C.

Foliage description:

*Arrangement.*—Opposite, simple.

*Length.*—About 5.1 cm.

*Width.*—About 2 mm to 3 mm.

*Shape.*—Three-lobed; deeply dissected.

*Apex.*—Broadly acute to slightly rounded.

*Base.*—Truncate.

*Margin.*—Entire.

*Texture, upper and lower surfaces.*—Smooth, glabrous.

*Venation pattern.*—Pinnate.

*Color.*—Developing and fully expanded foliage, upper surface: Close to 146A; venation, close to 146A. Developing and fully expanded foliage, lower surface: Close to 146B; venation, close to 146B.

*Petiole length.*—About 1.1 cm.

*Petiole diameter.*—About 2 mm.

*Petiole texture, upper and lower surfaces.*—Smooth, glabrous.

*Petiole color, upper surface.*—Close to 146B.

*Petiole color, lower surface.*—Close to 146C.

Inflorescence description:

*Appearance.*—Single terminal and axillary inflorescences with ray and disc florets. Inflorescences positioned above and beyond the foliage on moderately strong peduncles. Inflorescences face upright to outward. Freely flowering habit; about 24 inflorescences developing per lateral branch. Inflorescences persistent.

*Fragrance.*—None detected.

*Time to flower.*—Under natural season conditions, plants flower throughout the summer in Lancaster, Pa.

*Post-production longevity.*—Inflorescences maintain good substance for about five to seven days on the plant.

*Inflorescence bud.*—Height: About 7 mm. Diameter: About 7 mm. Shape: Globular. Color: Close to 5A.

*Inflorescence size.*—Diameter: About 2.4 cm. Depth (height): About 8 mm. Disc diameter: About 8 mm. Receptacle diameter: About 6 mm. Receptacle height: About 3 mm.

*Ray florets.*—Shape: Narrowly spatulate. Length: About 1.1 cm. Width: About 8 mm. Apex: Emarginate; ragged appearance. Base: Attenuate. Texture, upper and lower surfaces: Smooth, glabrous; slightly longitudinally ridged. Number of ray florets per inflorescence: About eight arranged in a single whorl. Aspect: Flat; reflexing with development. Color: When opening, upper surface: Towards the apex, close to 7B; towards the base, close to 183A. When opening, lower surface: Towards the apex, close to 5B; towards the base, close to 174A to 174B. Fully developed, upper surface: Towards the apex, close to 9A; towards the base, close to 185A. When opening, lower surface: Towards the apex, close to 9C; towards the base, close to 165C.

*Disc florets.*—Shape: Tubular; apex dentate. Length: About 5 mm. Diameter: About 1 mm. Number of disc florets per inflorescence: About 350. Color, immature: Apex: Darker than 183A. Mid-section: Close to 166C. Base: Close to 15B. Color, mature: Apex: Close to 183A. Mid-section: Close to 166D. Base: Close to 15D.

*Phyllaries.*—Quantity per inflorescence: About eight in two whorls. Length: About 7 mm. Width: About 3 mm. Shape: Elliptical. Apex: Acute. Base: Truncate. Margin: Entire. Texture, upper and lower surfaces: Smooth, glabrous. Color, upper surface: Close to 148A. Color, lower surface: Close to 146A.

*Peduncles.*—Length: About 8.2 cm. Diameter: About 7 mm. Strength: Moderately strong. Aspect: Mostly upright to about 45° from vertical. Texture: Smooth, glabrous. Color: Close to 146A.

*Reproductive organs.*—Androecium: Quantity per disc floret: Five. Anther shape: Linear. Anther length: About 2 mm. Anther color: Close to 185A. Filament length: About 3 mm. Filament color: Close to 183D. Pollen amount: Scarce. Pollen color: Close to 23A. Gynoecium: Quantity per disc floret: One. Pistil length: About 7 mm. Stigma shape: Cleft. Stigma color: Close to 26A. Style length: About 4 mm. Style color: Close to 26C. Ovary color: Close to 157B.

*Seed/fruit.*—Seed and fruit production has not been observed.

Disease/pest resistance: Plants of the new *Coreopsis* have not been shown to be resistant to pathogens and pests common to *Coreopsis*.

Garden performance: Plants of the new *Clematis* have exhibited good tolerance to rain and wind and have been observed to tolerate temperatures from about −3° C. to about 30° C.

It is claimed:

1. A new and distinct *Coreopsis* plant named 'Coreopram' as illustrated and described.

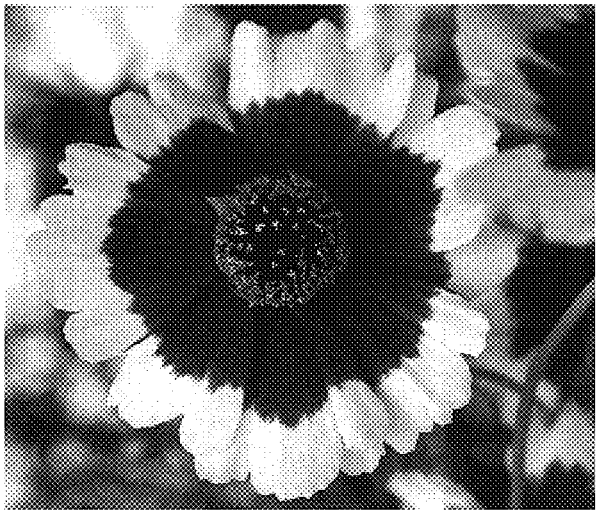
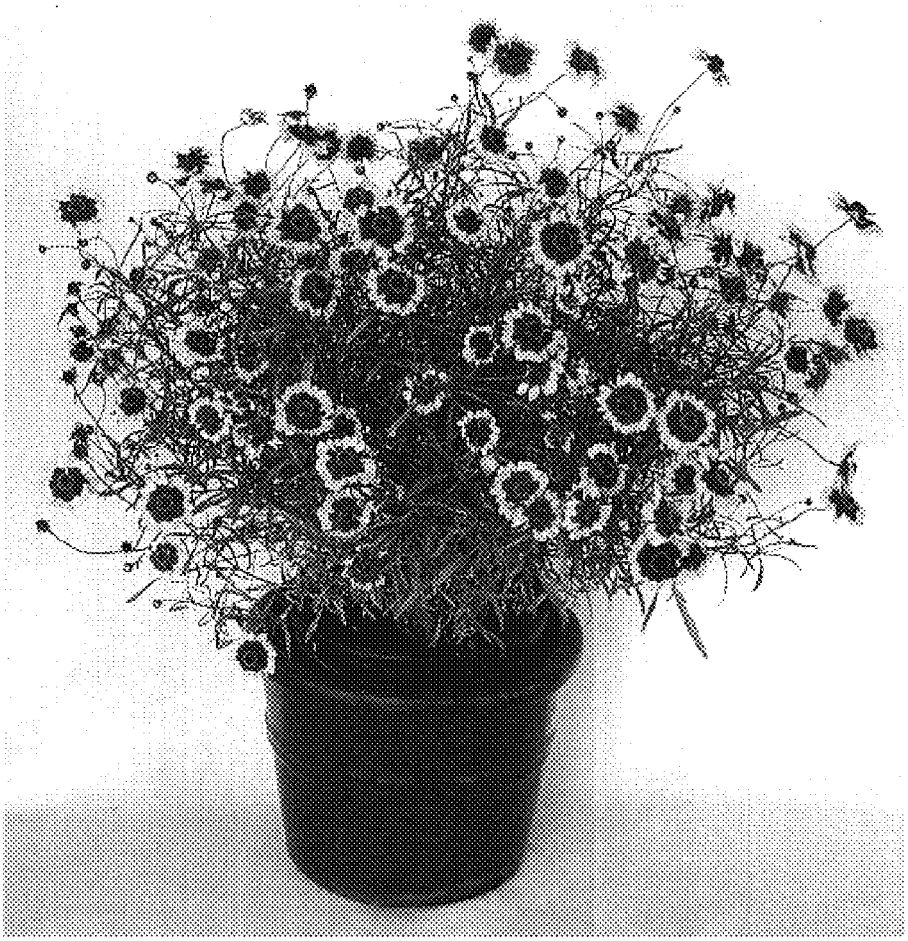

* * * * *